(12) United States Patent
Suehira (10) Patent No.: US 10,537,249 B2
(45) Date of Patent: Jan. 21, 2020

(54) SIGNAL PROCESSING METHOD, ACOUSTIC WAVE PROCESSING APPARATUS, AND RECORDING MEDIUM

(71) Applicant: CANON KABUSHIKI KAISHA, Tokyo (JP)

(72) Inventor: Nobuhito Suehira, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 724 days.

(21) Appl. No.: 14/948,096

(22) Filed: Nov. 20, 2015

(65) Prior Publication Data

US 2016/0150971 A1 Jun. 2, 2016

(30) Foreign Application Priority Data

Nov. 28, 2014 (JP) .................... 2014-242465

(51) Int. Cl.
*A61B 5/055* (2006.01)
*A61B 5/00* (2006.01)

(52) U.S. Cl.
CPC ............ *A61B 5/0095* (2013.01); *A61B 5/725* (2013.01); *A61B 2576/00* (2013.01)

(58) Field of Classification Search
CPC ... A61B 2576/00; A61B 5/004; A61B 5/0095; A61B 5/7203; A61B 5/725; A61B 8/0825; A61B 8/4494; A61B 8/5207; A61B 8/5269
See application file for complete search history.

(56) References Cited

U.S. PATENT DOCUMENTS

| 5,107,310 A | * | 4/1992 | Grudkowski | .......... H03K 19/08 257/241 |
| 2008/0173093 A1 | * | 7/2008 | Wang | ................... A61B 5/0073 73/602 |
| 2012/0136255 A1 | * | 5/2012 | Fan | ...................... A61B 8/0833 600/443 |
| 2013/0317325 A1 | * | 11/2013 | Wood | ................ A61B 5/14551 600/310 |
| 2014/0100438 A1 | | 4/2014 | Wada | |

FOREIGN PATENT DOCUMENTS

| CN | 103845078 A | 6/2014 |
| CN | 104107068 A | 10/2014 |
| JP | 2011-00414 A | 1/2011 |
| JP | 2012055692 A | 3/2012 |
| WO | 2014/093577 A1 | 6/2014 |
| WO | 2014/144257 A1 | 9/2014 |

* cited by examiner

*Primary Examiner* — Mark D Remaly
(74) *Attorney, Agent, or Firm* — Canon U.S.A., Inc. IP Division (57) ABSTRACT

A signal processing method for a plurality of reception signals, wherein a plurality of reception elements are each configured to receive acoustic waves and output a reception signal at a plurality of sampling times, includes generating a representative value signal from the plurality of reception signals, except for reception signals having amplitudes that are larger than a threshold value among the plurality of reception signals at each sampling time, generating a plurality of differential signals indicating differences between the plurality of reception signals obtained at each sampling time and the representative value signal, and generating image data using the plurality of differential signals.

20 Claims, 6 Drawing Sheets

SIGNAL PROCESSING METHOD, ACOUSTIC WAVE PROCESSING APPARATUS, AND RECORDING MEDIUM

BACKGROUND OF THE INVENTION

Field of the Invention

The present invention relates to a signal processing method, an acoustic wave processing apparatus, and a recording medium.

Description of the Related Art

As one of optical imaging techniques, photoacoustic tomography (PAT) has been widely used. In the photoacoustic tomography, a subject is irradiated with pulsed light so that acoustic waves generated in an inside of the subject are detected, and signals of the acoustic waves are analyzed so that information on optical characteristic values in the inside of the subject is visualized.

Imaging of comparatively-thin blood vessels, which form a tumor, has been attempted using a PAT apparatus for measurement of a living body. However, acoustic waves generated from these thin blood vessels and reception signals obtained by detection elements are comparatively weak, and an image of desired quality may not be obtained unless noise and any artifact are appropriately removed. An artifact means an image which appears as if something exists although nothing exists in practice.

One of the techniques of removing artifacts is disclosed in Japanese Patent Laid-Open No. 2011-00414. In the disclosure, removal of artifacts caused by a transient response due to interface acoustic waves is to be attained. A plurality of reception signals obtained at the same time point are added to one another, a signal obtained by the addition is standardized using a maximum amplitude, among amplitudes of the plurality of reception signals, as a reference, and thereafter, the signal is subtracted from the reception signals.

SUMMARY OF THE INVENTION

However, although Japanese Patent Laid-Open No. 2011-00414 discloses reduction of artifacts caused by a large signal generated due to a transient response, in-phase noise is not taken into consideration. In general, the in-phase noise is a signal having amplitude which is sufficiently small relative to the transient response caused by interface acoustic waves.

According to an embodiment of the present invention, there is provided a signal processing method of the present invention for a plurality of reception signals, wherein a plurality of reception elements are each configured to receive acoustic waves and output a reception signal at a plurality of sampling times, includes generating a representative value signal from the plurality of reception signals, except for reception signals having amplitudes that are larger than a threshold value among the plurality of reception signals at each sampling time, generating a plurality of differential signals indicating differences between the plurality of reception signals obtained at each sampling time and the representative value signal, and generating image data using the plurality of differential signals.

According to another embodiment of the present invention, there is provided an acoustic wave processing apparatus including a plurality of reception elements each configured to receive acoustic waves and output a reception signal at a plurality of sampling times, and a signal processing unit configured to process the plurality of reception signals. The signal processing unit is further configured to generate a representative value signal from the plurality of reception signals, except for reception signals having amplitudes that are larger than a threshold value among the plurality of reception signals at each sampling time, generate a plurality of differential signals indicating differences between the plurality of reception signals obtained at each sampling time and the representative value signal, and generate image data using the plurality of differential signals.

According to a further embodiment of the present invention, there is provided an acoustic wave processing apparatus including a plurality of reception elements each configured to receive acoustic waves and output a reception signal at a plurality of sampling times, a reference reception element configured not to receive the acoustic waves and configured to output a reference signal, and a signal processing unit configured to process the plurality of reception signals and the reference signal. The signal processing unit is further configured to generate differential signals indicating differences between the plurality of reception signals obtained at each sampling time and the reference signal, and generate image data from the differential signals.

Further features of the present invention will become apparent from the following description of embodiments with reference to the attached drawings. Each of the embodiments of the present invention described below can be implemented solely or as a combination of a plurality of the embodiments or features thereof where necessary or where the combination of elements or features from individual embodiments in a single embodiment is beneficial.

DESCRIPTION OF THE EMBODIMENTS

First Embodiment

A first embodiment of the present invention will be described taking an acoustic wave processing apparatus having an arc-type transducer including a plurality of reception elements arranged in an arc shape as an example. The acoustic wave processing apparatus according to this embodiment is a photoacoustic wave processing apparatus, which receives acoustic waves (typically, ultrasonic waves) generated in a subject by irradiating the subject with pulsed light.

System Configuration

Figure 1:
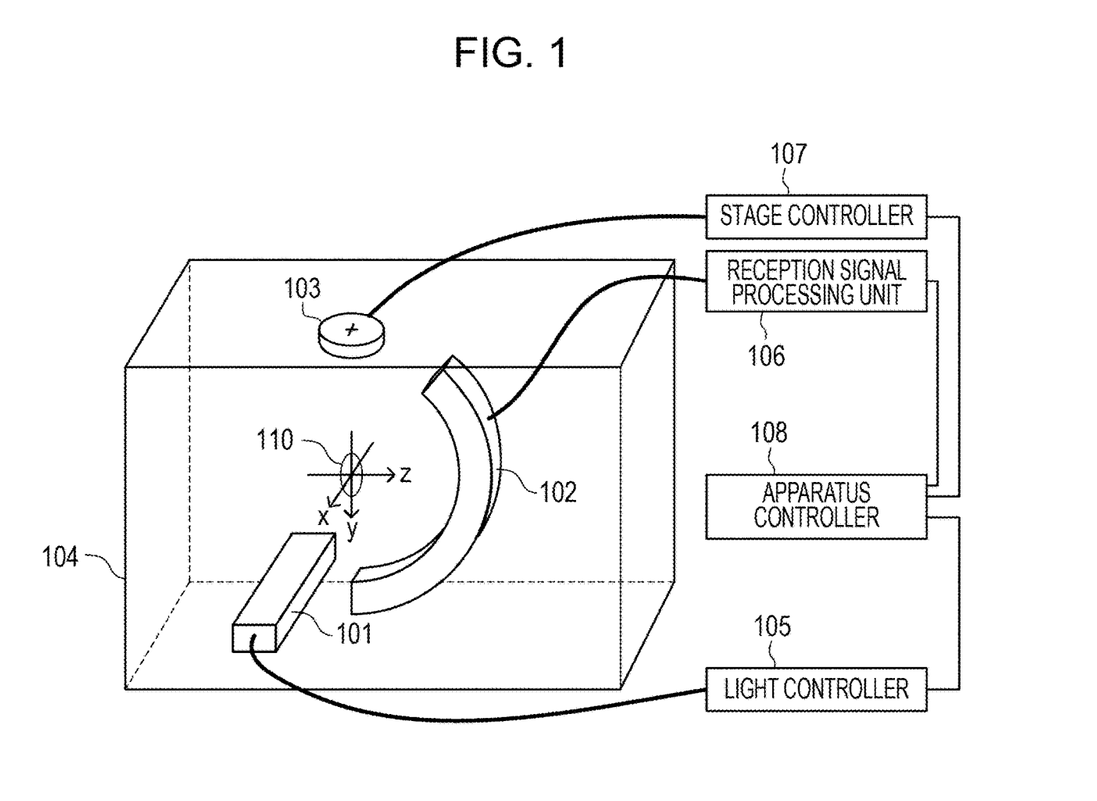
FIG. 1 is a diagram illustrating a configuration of an acoustic wave processing apparatus according to a first embodiment of the present invention.

FIG. 1 is a diagram illustrating a configuration of the acoustic wave processing apparatus of this embodiment. The acoustic wave processing apparatus includes a light irradiation unit 101, a transducer 102, a stage 103, a light controller 105, a reception signal processing unit 106, a stage controller 107, and an apparatus controller 108. A coordinate system used in this embodiment has a center of the arc of the transducer 102 as a reference, and the stage 103 rotates in an x-z plane about a y axis. The light irradiation unit 101 irradiates an origin of a coordinate with light along an x axis.

A subject 110 may be rotated by the stage 103 about the y axis. The subject 110 may be held in a state in which the subject 110 is hung from the stage 103. When the light irradiation unit 101 irradiates the subject 110 with light while the subject 110 is rotated by the stage 103, signals may be obtained from all directions of the subject 110. Note that the subject 110 and the transducer 102 are disposed in a water tank 104. Furthermore, since the water tank 104 is filled with water, generated acoustic waves are sufficiently transmitted. A substance which fills the water tank 104 is not limited to water, and any substance may be used as long as the substance may transmit acoustic waves generated from the subject 110 to the reception elements included in the transducer 102.

The components included in the acoustic wave processing apparatus will now be described further in detail.

Light Irradiation Unit and Light Controller

The light irradiation unit 101 irradiates the subject 110 with light under control of the light controller 105. In this embodiment, the subject 110 is irradiated with light from a positive direction of the x axis. The light irradiation unit 101 includes a light source which generates light and a light guiding member which guides the generated light so that the subject 110 is irradiated with the light. The light source is preferably a laser light source so that large output is obtained. However, a light emitting diode, a flash lamp, or the like may be used as the light source instead of the laser light source. When a laser is to be used, various lasers, such as a solid-state laser, a gas laser, a dye laser, and a semiconductor laser, may be used. A timing, a waveform, intensity, and the like of the irradiation are controlled by the light controller 105. It is not required that the subject 110 is irradiated from a certain direction, and the subject 110 may be irradiated from a plurality of directions so that a blind area is not generated. Specifically, a plurality of emission terminals of the light irradiation unit 101 may be provided or a plurality of light irradiation units 101 may be provided.

To effectively generate photoacoustic waves which are a type of acoustic wave, the light controller 105 irradiates the subject 110 with pulsed light in a sufficiently short period of time in accordance with a thermal characteristic of the subject 110. It is preferable that, if the subject 110 is a living body, a pulse width of pulsed light generated by the light irradiation unit 101 is approximately 10 to 50 nanoseconds. Furthermore, it is preferable that a wavelength of the pulsed light is sufficient for transmission of light to an inside of the subject 110. Specifically, in a case of a living body, the wavelength is equal to or larger than 700 nm and equal to or smaller than 1100 nm. It is assumed here that a titanium-sapphire laser, which is a solid-state laser, having a wavelength of 800 nm, is used in this embodiment.

Transducer and Reception Signal Processing Unit

Acoustic waves generated in a light absorbent in the subject 110 are received by the transducer 102. The transducer 102 of this embodiment is an arc type ultrasonic wave transducer including a plurality of reception elements arranged on an arc having the origin of the coordinate axis as a center. The acoustic waves received by the reception elements are converted into analog electric signals. Examples of the elements which have such a function include piezoelectric ceramics (piezoelectric transducer: PZT) and a capacitive micromachined ultrasonic transducer (CMUT). Furthermore, the reception elements preferably have high sensitivity and a large frequency band. It is assumed that a radius of the arc of the transducer 102 of this embodiment is 60 mm, an opening has 150 degrees, and the number of reception elements is 64. However, the embodiment is not limited to these values.

The signals converted into the electric signals are transmitted to the reception signal processing unit 106 which performs amplification, AD conversion, and the like on the electric signals so as to obtain digital signals. The digital signals are transmitted to the apparatus controller 108. A timing when the acoustic waves are received is controlled by the apparatus controller 108 so as to be synchronized with the light irradiation performed by the light irradiation unit 101. The reception elements of the transducer 102 have sensitivity in a band from 2 MHz to 5 MHz, for example. Furthermore, a sampling frequency (rate) at least satisfies sampling theorem relative to a maximum frequency in a band of a signal to be detected by the transducer 102. In this embodiment, sampling is performed 2048 times at a sampling rate of 50 MHz. A starting time of a period in which the sampling is performed may be set taking a delay time from when the irradiation with pulsed light is started to when the pulsed light reaches the transducer 102 into consideration. Meanwhile, the sampling may be continuously performed after the timing of the irradiation with pulsed light and only data based on the photoacoustic waves may be extracted from among sampled data. Furthermore, each of the digital signals has 12 bits including a sign. Specifically, 1 bit is used for a sign and the remaining 11 bits represent amplitude of a reception signal. The reception signal processing unit 106 may include, in addition to an amplifier and an A/D conversion unit, a storage unit which temporarily stores the reception signals.

Apparatus Controller

The apparatus controller 108 functioning as a signal processing unit performs image reconstruction in accordance with instructions for reception control of the light irradiation unit 101 and the transducer 102 and the reception signals. Specifically, the apparatus controller 108 generates image data of the subject 110. Furthermore, the apparatus controller 108 includes user interfaces, and may perform a change of a measurement parameter, start and stop of measurement, a selection of an image processing method, storage of subject information and an image, data analysis, and the like. Furthermore, reconstructed image data is displayed in a display unit (not illustrated) as a three-dimensional tomographic image, for example. Note that the signal processor may be configured as a computer which is independent from the apparatus controller 108 and which includes a CPU, a main storage device, and an auxiliary storage device in order to perform high-speed processing, or may be designed as dedicated hardware.

Signal Processing Step

Figure 2:
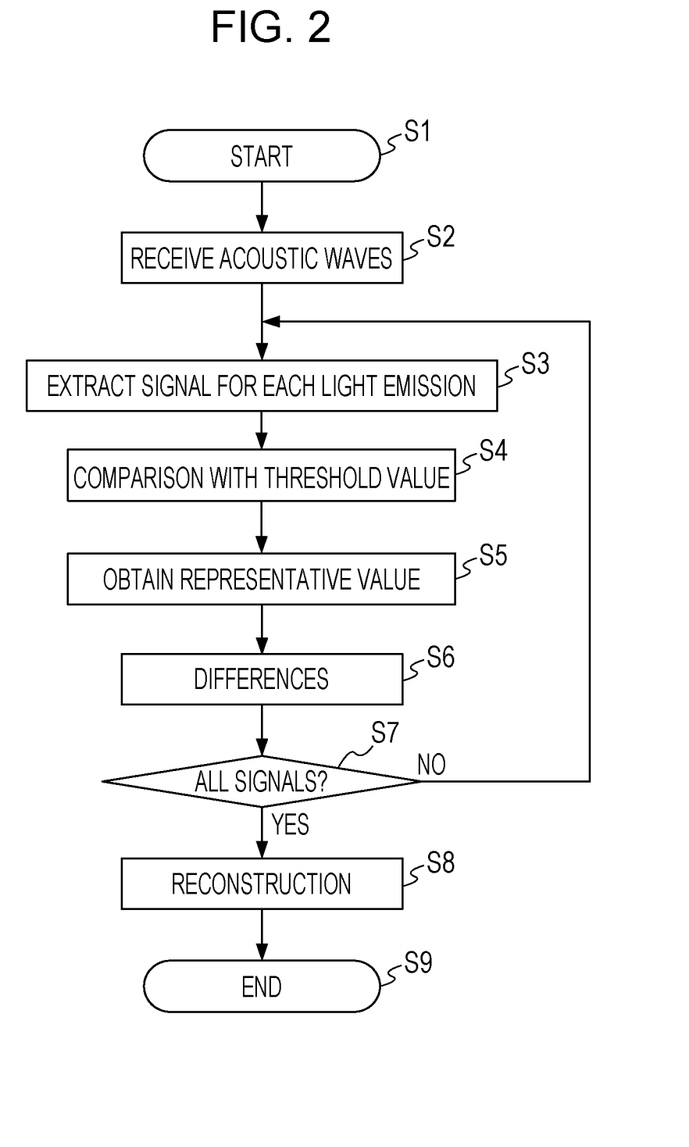
FIG. 2 is a flowchart illustrating a signal process according to the embodiments of the present invention.

FIG. 2 is a flowchart illustrating a flow of a signal process according to this embodiment.

Measurement is started in step S1. Light irradiation is performed while a direction of the subject 110 is changed by rotating the subject 110 using the stage 103, and acoustic waves generated by the irradiation of the subject 110 with the pulsed light from various angles are measured. Here, the measurement is performed every time the subject 110 is rotated by 4 degrees in the x-z plane, and all around the subject 110 is measured by performing the measurement 90 times in total. Data obtained at the various angles are successively stored in the reception signal processing unit 106 on a temporary basis. When the measurements in all measurement positions (90 measurements) are terminated, two-dimensional arrangement data including the data measured at the various angles may be obtained. Then the two-dimensional arrangement data is transmitted to the apparatus controller 108. A size of the two-dimensional arrangement in this case is 5760×2048 (90 (the number of times the measurement is performed)×64 (the number of elements)×2048 (the number of samples per measurement)). Since amplitudes (that is, signal intensity) of the acoustic waves are changed with time, a number of samples are obtained per measurement in a sampling cycle which is sufficient for restoring waveforms of the acoustic waves so that a plurality of reception signals are generated.

Figure 3:
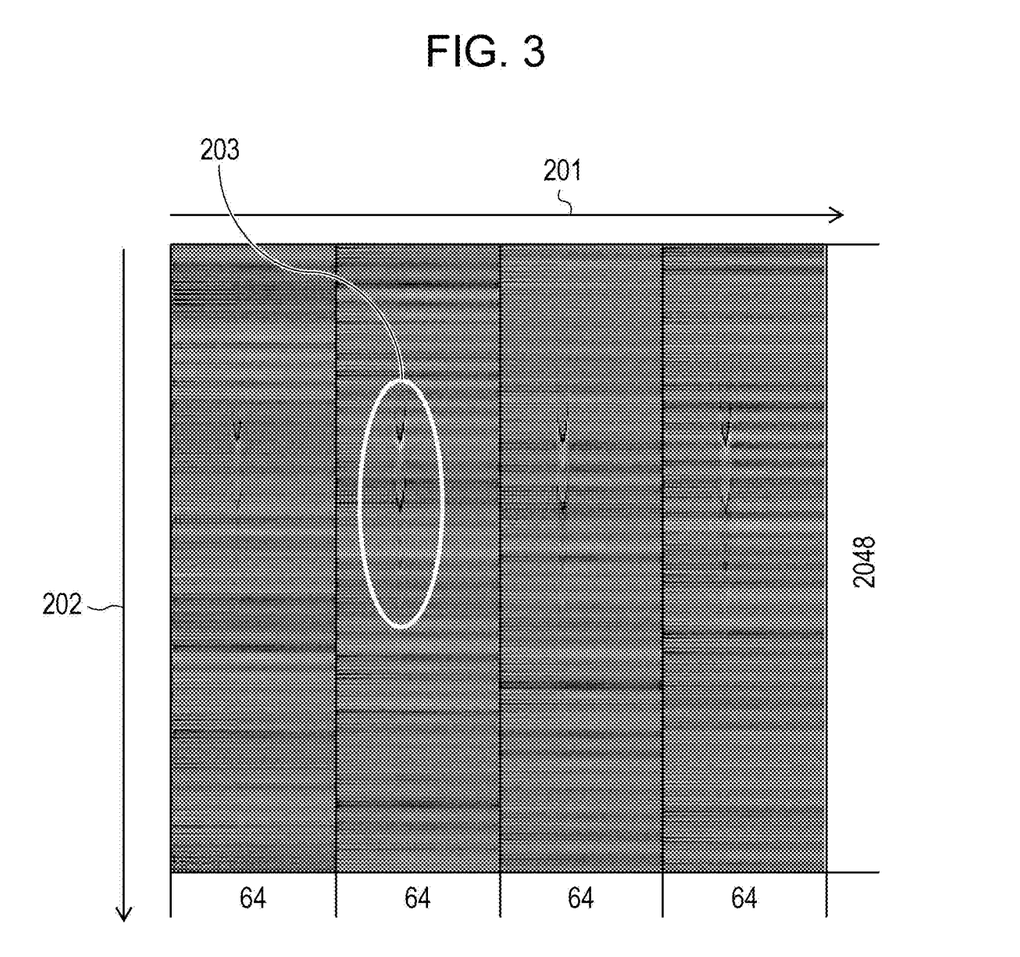
FIG. 3 is a diagram illustrating reception signals according to the embodiments of the present invention.

In step S2, the apparatus controller 108 receives the measurement data which is temporarily stored in the reception signal processing unit 106. Here, an example of the measurement data received by the apparatus controller 108 is illustrated in FIG. 3. The subject 110 of this embodiment is a cylindrical transparent tube which has a bore diameter of 1 mm and which includes dilute India ink encapsulated therein. The transducer 102 is an arc type ultrasonic transducer. In this embodiment, only measurement data at measurement angles in four positions are visualized. Density of the data indicates magnitudes of values. It is assumed here that a periphery of the tube is filled with water, and an object serving as a sound source of acoustic waves by absorbing light does not exist.

In FIG. 3, data corresponding to the 64 elements exist in a direction indicated by an arrow mark 201 in each of the four measurements. Here, data corresponding to light irradiation performed four times at different angles is illustrated. On the other hand, in a direction indicated by an arrow mark 202, 2048 data samples obtained at a sampling rate of 50 MHz in an elapsed time using a light irradiation time as a reference are arranged. Bands extending along the arrow mark 201 mean that inputs having approximately the same magnitude are performed on the plurality of reception elements at a certain time point, and the bands correspond to the in-phase noise. Amplitude of the in-phase noise is approximately +20 in a signed 12-bit digital signal, for example. Furthermore, intensities of the in-phase noises generated in light irradiation performed four times are different from one another. Furthermore, the in-phase noise is not generated in a fixed cycle. Note that it is estimated that the in-phase noise is electrical noise input through the water. For example, it is estimated that the in-phase noise is generated when electromagnetic waves propagate through the water, or when a change of a water pressure due to vibration of the water is detected by the transducer 102. Furthermore, in a case where the plurality of reception elements are connected to a common reference power source (GND), noise which is mixed in GND may become the in-phase noise.

In step S3, data signals for each measurement position are extracted from the 5760×2048 data obtained in step S2. The extracted data is two-dimensional data (64×2048) obtained at each measurement position (e.g. 2048 samples from the 64 elements at a single measurement position). The data extracted in step S3 are to be used in step S4 and step S6.

In FIG. 3, wedge shaped marks are recognized in a region denoted by a reference numeral 203. These are the reception signals based on the acoustic waves. Therefore, in step S4, a process of determining reception signals from among the digital signals at the various time points (e.g. at each of the 2048 samplings) is performed. As a concrete method for the process, each of the digital signals extracted at each measurement position in step S3 is compared with a threshold value. If a magnitude of a digital signal exceeds the threshold value, information indicating that the digital signal exceeds the threshold value is stored in a memory included in the apparatus controller 108, such that the digital signal is indicated as being a reception signal. The information may be stored separately from the two-dimensional arrangement data described above, or flags indicating magnitudes relative to the threshold value may be added to the elements included in the two-dimensional arrangement data. The threshold value is approximately 25 as an absolute value, for example. In a case of signed 12-bit signals, for example, digital signals equal to or larger than +25 and equal to or smaller than −25 are determined as reception signals based on the acoustic waves. In a case where an offset is included in the digital signals, the threshold value is set using a value of the offset as a reference.

In step S5, a representative value signal, which is a representative value of the digital signals except for the reception signals determined in step S4, among the digital signals obtained at the same time point (e.g. at each of the 2048 samplings) is generated. Here, among data obtained from the 64 elements at a certain time point, data except for data that exceeded the threshold value in step S4 (e.g. the reception signals) are averaged so that a representative value signal at each time point is generated. By this, even when random noise is generated, the influence of random noise may be reduced. This process is performed for the sampling performed 2048 times whereby one-dimensional data of a representative value signal which is an average value of the digital signals except for the reception signals based on the acoustic waves may be obtained. In a case where all the signals obtained at the same time point have values that exceed the threshold value, it is determined that the in-phase noise is not generated. Furthermore, it is not necessarily the case that, when the representative value signal is to be generated, among the data obtained from the 64 elements at the same time point, all the data except for the data that exceeds the threshold value are used. Some of the data, except for the data that exceeds the threshold value, may be averaged and an obtained value may be determined as the representative value signal.

In step S6, an in-phase noise component is removed from the signals. This is realized by subtracting the one-dimensional data of 1×2048 obtained in the process in step S5 from the two-dimensional arrangement data of 64×2048 described in step S3 for each element. Specifically, a process of subtracting, from each of the 64 data which are sampled at the respective time points, the data of the mean value obtained in step S5 at a corresponding one of the time points is performed.

In step S7, it is determined whether signals relative to all the light irradiation have been processed. When it is determined that the process has been performed on all the signals, the process proceeds to step S8. On the other hand, when at least one of the signals has not been processed, the process returns to step S3 where a signal of the next light irradiation is processed. After all the signals are processed, two-dimensional arrangement data of 5760×2048 from which the in-phase noise is removed is obtained.

Figure 4A:
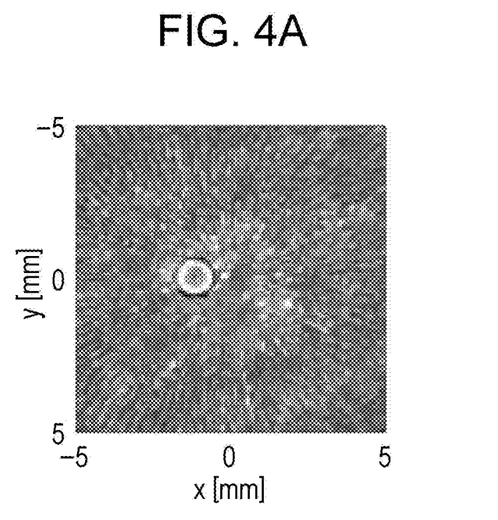
FIGS. 4A to 4D are diagrams illustrating comparison among images which have not been subjected to the signal process and images which have been subjected to the signal process according to the embodiments of the present invention.
Figure 4B:
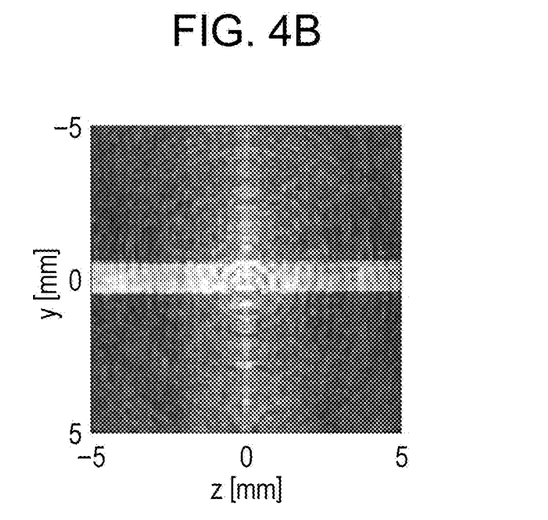
Figure 4C:
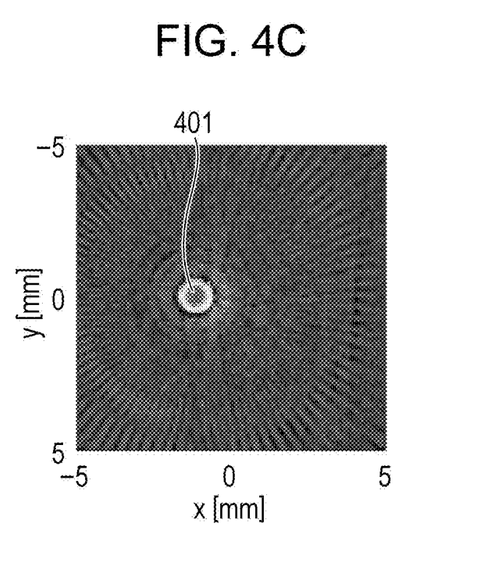
Figure 4D:
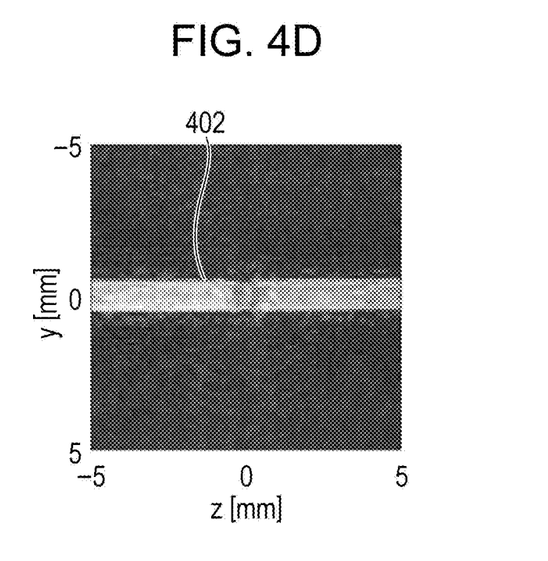

In step S8, reconstruction, that is, generation of image data, is performed using the data from which the in-phase noise is removed. Examples of a method for the image reconstruction include a Fourier transform method, a universal back-projection method, and a filtered back-projection method. Here, a difference between a reconstructed image which has not been subjected to the process of this embodiment, and a reconstructed image which has been subjected to the process of this embodiment will be described with reference to FIGS. 4A to 4D. FIG. 4A is a diagram illustrating a maximum intensity projection (MIP) image in an x-y plane obtained when the process of this embodiment is not performed, and FIG. 4B is a diagram illustrating an MIP image in a y-z plane obtained when the process of this embodiment is not performed. An MIP image in a certain plane is an image constructed by extracting a signal having a maximum value in a direction orthogonal to the certain plane. For example, the MIP image in the x-y plane is constructed by extracting a signal having a maximum value in a z axis direction among data constituting a three-dimensional image. FIG. 4C is a diagram illustrating an MIP image in the x-y plane obtained when the process of this embodiment is performed, and FIG. 4D is a diagram illustrating an MIP image in the y-z plane obtained when the process of this embodiment is performed. In FIGS. 4A and 4B, the in-phase noise has not been removed, and therefore, the images are displayed as if a sound source exists although a sound source is not provided near the tube, and the tube is mixed in noise. On the other hand, in FIGS. 4C and 4D, the in-phase noise has been removed, and therefore, a portion around the tube is represented by a dark color near black. Accordingly, it is recognized that the tube is distinguishable from a background. Specifically, contrast between the background and the tube is high. Note that, although the tube is filled with the dilute India ink, a hollow-like tube is observed since the reception elements which do not have sensitivity in a region of comparatively low frequencies are used.

In step S9, the series of processes is terminated.

As described above, by the process according to this embodiment, an image in which the in-phase noise is reduced may be obtained.

Although a relative position between the subject 110 and the transducer 102 is changed by rotating the subject 110 relative to the transducer 102 using the stage 103, the relative position may be changed by changing a position of the transducer 102 while the subject 110 is fixed.

In this embodiment, the case where the threshold value is a digital value of 25 when the digital signals are represented by signed 12 bits is described as an example. Since one of the 12 bits is a sign representing positive or negative, signals included in a range of $25/(2^{11}) \approx 1.2\%$ relative to a maximum value, or a minimum value of the digital values, are determined to be smaller than the threshold value. However, the threshold value is not limited to this, and it can be appropriately set in accordance with estimated magnitudes of the reception signals. If the threshold value is too large, a signal to be used for the image reconstruction is processed as noise whereas if the threshold value is too small, a signal to be processed as noise is used for the image reconstruction, and accordingly, quality of an obtained image is degraded. Therefore, it is preferable that the threshold value is set to be a value equal to or larger than 1% and equal to or smaller than 10% relative to a maximum amplitude of the digital signals or the reception signals.

Furthermore, the case where the reception signals having amplitudes equal to or smaller than the threshold value are averaged so that the in-phase noise is calculated has been described. However, instead of the averaging, reception data having a median value or a mode value among the reception signals having amplitudes equal to or smaller than the threshold value may be determined as the in-phase noise. Specifically, a representative value signal is generated from a plurality of reception signals except for reception signals having amplitudes larger than the threshold value, and image construction is performed using subtracted signals (differential signals) obtained by subtracting the representative value signal from the reception signals so that the in-phase noise is reduced. Note that the averaging is preferably employed as a method for generating a representative value signal in terms of reduction of random noise.

In a case where, unlike the process of this embodiment, all the signals obtained at the same time point are averaged without excepting the reception signals based on the acoustic waves having high intensity, signals are generated in positions where signals are not to be generated when differences are calculated in a later process, and therefore, artifacts are generated. Conversely, in a case where small signals which are not noise are mixed, the small signals may be ignored by the averaging. By performing the process in step S4, data which stores positions of the signals having high intensity and positions of signals which do not have high intensity may be obtained.

Second Embodiment

In a second embodiment, an acoustic wave tomographic diagnosis apparatus for a breast using reception elements arranged in an inner wall of a hemispherical container will be described as an example of an acoustic wave processing apparatus. Here, portions different from the first embodiment will be mainly described.

Figure 5A:
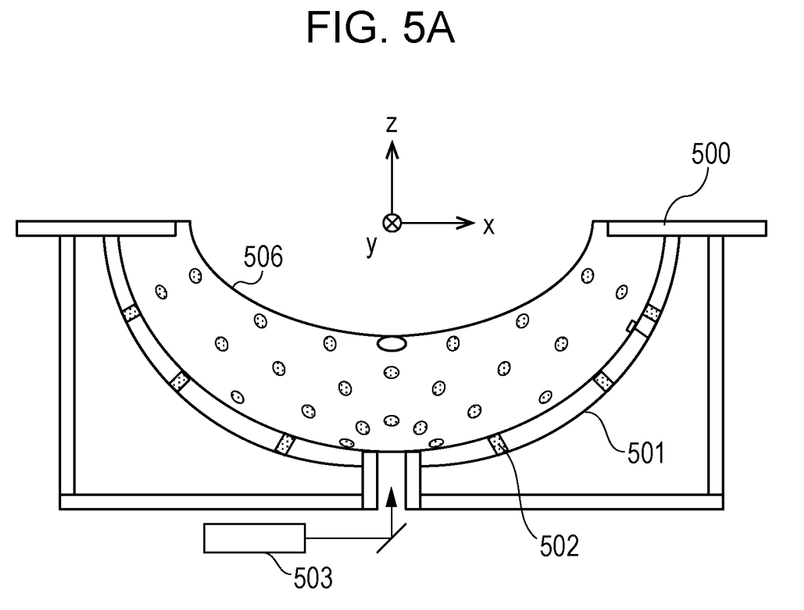
FIGS. 5A and 5B are diagrams illustrating arrangement of reception elements according to a second embodiment of the present invention.
Figure 5B:
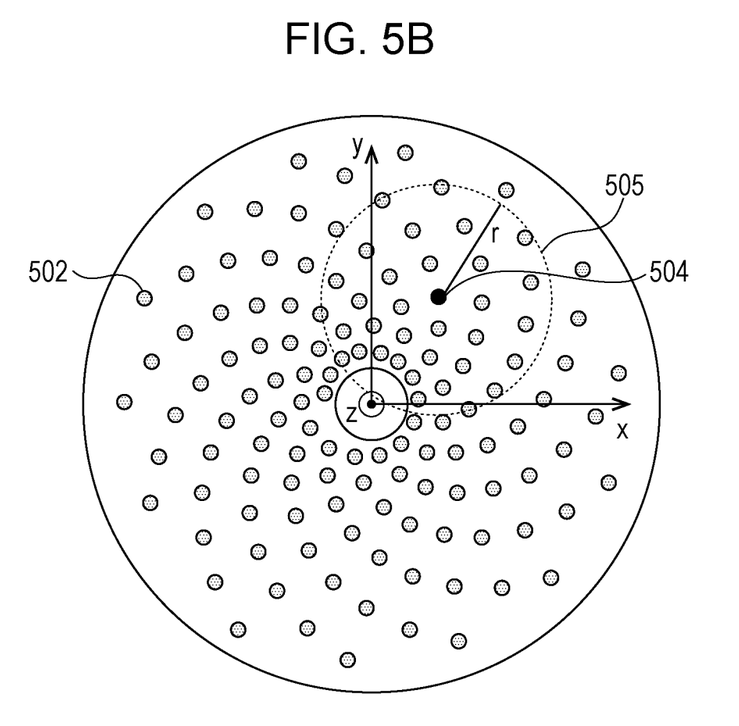

A portion of the acoustic wave tomographic diagnosis apparatus of this embodiment is illustrated in FIGS. 5A and 5B. FIG. 5A is a sectional view illustrating a configuration of a portion which holds a subject in the acoustic wave tomographic diagnosis apparatus. This cross-sectional surface is determined as an x-z plane. As illustrated in FIG. 5A, a support base 500 which supports a subject 506 includes an opening to which the subject 506 is to be inserted. A hemispherical container 501 is disposed so as to cover the opening and reception elements 502 are disposed along a surface of the container 501. In other words, the plurality of reception elements 502 are disposed on a half sphere. A portion between the container 501 and the subject 506 is filled with solution serving as a matching layer for obtaining acoustic matching between the subject 506 and the reception elements 502. The solution is typically water. Furthermore, a cup may be disposed in a portion between the subject 506 and the reception elements 502 so as to restrict a shape of the subject 506. Any material may be used for the cup as long as the material is transparent relative to light and does not disturb measurement of acoustic waves. If the cup is to be used, a matching agent for the acoustic matching may be disposed in a portion between the cup and the subject 506. Furthermore, the hemispherical container 501 has an opening which allows light emitted from a light irradiation unit 503 to pass. Accordingly, the subject 506 may be irradiated with light from a negative direction to a positive direction of a z axis.

A portion of the subject 506 to be measured, that is, a breast, for example, is inserted into the opening of the support base 500 in a prone position. A position of the container 501 relative to the subject 506 may be changed by moving the container 501 by an XY stage, not illustrated, in an x-y plane. Then, the subject 506 is irradiated with pulsed light emitted from the light irradiation unit 503 while the XY stage is scanned, and generated acoustic waves are detected by the reception elements 502. Data thus obtained is reconstructed so that a three-dimensional acoustic wave image is obtained.

FIG. 5B is a diagram illustrating the container 501 viewed from a positive direction in the z axis. In this embodiment, 128 reception elements 502 are spirally arranged along a hemisphere face. Note that the arrangement of the reception elements 502 is not limited to the spiral arrangement nor the number (128) of reception element, and the reception elements 502 may be arranged in a concentric fashion or other various fashions.

Also in this embodiment, a flow of a signal process is the same as that of the first embodiment. However, the flow of the signal process of this embodiment is different from that of the first embodiment in the processes in step S4 and step S5 since the reception elements 502 are spirally arranged and scanning is performed on the XY stage in this embodiment.

Since scanning is performed on the XY stage, the different reception elements may have different in-phase noises depending on positions of transducers, positions of the stage, and wiring of circuits in stages following the reception elements. For simplicity of description, here, a case where influence of in-phase noise is varied only depending on positions of the reception elements 502 in the hemispherical face of the hemispherical container 501 will be described.

In this embodiment, digital signals obtained from reception elements 502 positioned in a predetermined range including a target reception element 504 at a center thereof are referred to so that the in-phase noise is removed. For example, in FIG. 5B, in a case where the reception element 504 is determined as a target reception element, in projection in the x-y plane, digital signals obtained from and the reception elements 502 included in a circle 505 having a diameter r from the reception element 504 are referred to. A process the same as that of the first embodiment is performed on data obtained from the reception elements 502 included in the circle 505. Specifically, a representative value signal is calculated from data except for data having amplitudes larger than a threshold value and determined as reception data, and is determined as the in-phase noise of reception signals obtained from the reception elements 502 included in the circle 505. The in-phase noise thus obtained is subtracted from the reception data obtained from the target reception element 504 so that a subtracted signal (a differential signal) from which the in-phase noise is reduced is obtained. The same process is also performed on the other reception elements 502. In this way, an acoustic wave image in which the in-phase noise is reduced may be obtained.

Note that, when the in-phase noise is to be obtained, averaging is performed using the predetermined number of reception elements. For example, the XY plane is divided into regions by 90 degrees and an average of reception signals except for signals which exceed the threshold value among all reception elements included in each of the regions may be calculated. This method is effective in a case where a configuration of an electric circuit or a configuration of wiring is divided by 90 degrees or is divided into a plurality of channels. Furthermore, in this case, different threshold values may be set for the different regions.

Figure 6:
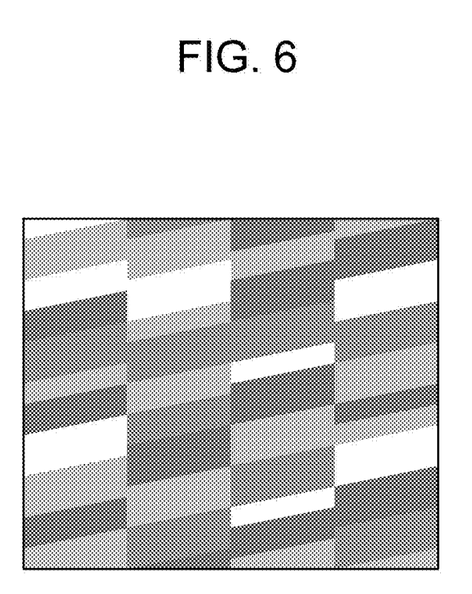
FIG. 6 is a diagram schematically illustrating a state of noise according to the second embodiment of the present invention.

Here, unlike the in-phase noise which reaches the plurality of reception elements at the same time point as illustrated in FIG. 3, the in-phase noise may be seen as bands diagonally extending as illustrated in FIG. 6. This is generated in a case where arrival times of in-phase components are different depending on positions of the reception elements. In this case, averaging is performed after data is corrected so that a difference between arrival times, that is, a difference between reception times, becomes small or is not detected. Thereafter, the in-phase noise is reduced in accordance with the arrival times for individual elements.

Furthermore, in a case where a frequency of the in-phase noise is within a certain band, a component of the in-phase noise may be extracted by a frequency filter process. By this process, even in a position in which the in-phase noise is determined not to be generated since it is determined that signal intensity is high, a value for maintaining continuity of a frequency may be assigned. Specifically, the in-phase noise included in a target reception element may be estimated from data obtained from reception elements near the target reception element.

Moreover, a reference reception element for obtaining only the in-phase noise may be disposed. Specifically, the reference reception element may be disposed in a direction in which acoustic signals generated by the subject 506 are not received. For example, the reception elements are arranged such that reception surfaces thereof which receive acoustic waves face the same direction or face the same region so that the reception elements have directionality whereas the reference reception element is arranged such that a reception surface thereof do not face the same direction or do not face the same region. Furthermore, the reference reception element may include an acoustic wave reduction member which reduces input of acoustic waves generated from the subject 506 as a mechanical part. Using a reference signal output from the reference reception element, the in-phase noise electrically supplied through water may be reduced.

In this embodiment, the case where the reception elements 502 are disposed along the hemispherical face of the hemispherical container 501 is described as an example. However, as with the first embodiment, the reception elements 502 may be arranged in an arc shape or arranged in a plane or in a one-dimensional shape.

In the foregoing embodiments, the case where signals having amplitudes equal to or smaller than the threshold value are averaged so that the in-phase noise is calculated is described as an example. However, reception signals having amplitudes equal to the threshold values may not be subjected to the averaging process. Specifically, the in-phase noise may be calculated by performing the averaging process on reception signals having amplitudes smaller than the threshold value. Furthermore, as with the first embodiment, it is not necessarily the case that a representative value signal is a mean value, and may be a median value or a mode value.

Furthermore, although the measurement of photoacoustic waves is taken as an example in the foregoing embodiments, the present invention is not limited to the measurement of photoacoustic waves. For example, the present invention is applicable to obtainment of an ultrasonic echo image based on acoustic waves obtained by reflecting ultrasonic waves in a subject. In this case, reception elements that may serve as transmission elements for transmitting ultrasonic waves, or transmission elements which are dedicatedly disposed for transmission of ultrasonic waves, may be used. In addition to the measurement of photoacoustic waves, measurement of acoustic waves by ultrasonic echo may be performed. In an ultrasonic apparatus which obtains an ultrasonic echo image, ultrasonic waves with which a subject is irradiated may be focused on a specific position, and meanwhile, in a case of the measurement of photoacoustic waves, acoustic waves are generated in an unspecified position in the subject where light is absorbed. Therefore, generation of image data based on the measurement of photoacoustic waves is likely to be vulnerable to noise when compared with generation of image data based on ultrasonic echo. Accordingly, the techniques of the foregoing embodiments especially have remarkable effects when being used in a photoacoustic wave reception apparatus. Furthermore, a plurality of elements of the embodiments may be combined or modified without departing from the present invention.

OTHER EMBODIMENTS

Embodiments of the present invention can also be realized by a computer of a system or apparatus, that reads out and executes computer executable instructions (e.g., one or more programs) recorded on a storage medium (which may also be referred to more fully as a 'non-transitory computer-readable storage medium'), to perform the functions of one or more of the above-described embodiments, and/or that includes one or more circuits (e.g., application specific integrated circuit (ASIC)) for performing the functions of one or more of the above-described embodiments, and by a method performed by the computer of the system or apparatus by, for example, reading out and executing the computer executable instructions from the storage medium to perform the functions of one or more of the above-described embodiments and/or controlling the one or more circuits to perform the functions of one or more of the above-described embodiments. The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to embodiments, it is to be understood that the invention is not limited to the disclosed embodiments. The scope of the following claims is to be accorded the broadest interpretation so as to encompass all such modifications and equivalent structures and functions.

This application claims the benefit of Japanese Patent Application No. 2014-242465, filed Nov. 28, 2014, which is hereby incorporated by reference herein in its entirety.

What is claimed is:

1. A method for a processing apparatus having a signal processor configured to process a plurality of reception signals, wherein each of a plurality of reception elements is configured to receive acoustic waves and extract and output a data signal at each of a plurality of sampling times as part of a plurality of data signals obtained at a same time, the method comprising:
generating one or more processed reception signals by removing, from among the plurality of data signals, a data signal having an amplitude that is larger than a threshold value, corresponding to each of the plurality of sampling times, wherein each removed data signal is part of the one or more processed reception signals;
generating a representative value signal as a representative value of data signals in the plurality of data signals that are other than the one or more processed reception signals;
generating a plurality of differential signals by calculating differences between the one or more processed reception signals and the representative value signal, corresponding to each of the plurality of sampling times; and
generating image data for a display using the plurality of differential signals.

2. The method according to claim 1, wherein generating the representative value signal includes generating the representative value signal by averaging the data signals in the plurality of data signals that are other than the one or more processed reception signals.

3. The method according to claim 1, wherein generating the representative value signal includes generating the representative value signal of less than all of the data signals in the plurality of data signals that are other than the one or more processed reception signals.

4. The method according to claim 1, wherein the acoustic waves are photoacoustic waves generated by irradiating a subject with the light.

5. The method according to claim 1, wherein the representative value signal is a signal having a median value or a mode value among the data signals in the plurality of data signals that are other than the one or more processed reception signals.

6. The method according to claim 1,
wherein the plurality of reception elements is arranged in an arc shape or a hemispherical shape, and
wherein the threshold value is equal to or larger than 1% and equal to or smaller than 10% of a possible maximum amplitude of the plurality of data signals.

7. The method according to claim 1, wherein the acoustic waves are ultrasonic waves which are transmitted and are reflected in a subject.

8. The method according to claim 1, wherein the signal processor is configured to add a flag indicating a magnitude relative to the threshold value to the one or more processed reception signals corresponding to each of the plurality of sampling times.

9. The method according to claim 1, wherein the same time is a same time point.

10. A non-transitory computer-readable storage medium storing a program to cause a computer to perform a method for a processing apparatus having a signal processor configured to process a plurality of reception signals, wherein each of a plurality of reception elements is configured to receive acoustic waves and extract and output a data signal at each of a plurality of sampling times as part of a plurality of data signals obtained at a same time, the method comprising:
generating one or more processed reception signals by removing, from among the plurality of data signals, a data signal having an amplitude that is larger than a threshold value, corresponding to each of the plurality of sampling times, wherein each removed data signal is part of the one or more processed reception signals;
generating a representative value signal as a representative value of data signals in the plurality of data signals that are other than the one or more processed reception signals;
generating a plurality of differential signals by calculating differences between the one or more processed reception signals and the representative value signal, corresponding to each of the plurality of sampling times; and
generating image data for a display using the plurality of differential signals.

11. A processing apparatus comprising:
a signal processor configured to process a plurality of reception signals, wherein each of a plurality of reception elements is configured to receive acoustic waves and extract and output a data signal at each of a plurality of sampling times as part of a plurality of data signals obtained at a same time; and memory storing instructions that, when executed by the signal processor, cause the processing apparatus to perform operations including:

generating one or more processed reception signals by removing, from among the plurality of data signals, a data signal having an amplitude that is larger than a threshold value, corresponding to each of the plurality of sampling times, wherein each removed data signal is part of the one or more processed reception signals, generating a representative value signal as a representative value of data signals in the plurality of data signals that are other than the one or more processed reception signals, generating a plurality of differential signals by calculating differences between the one or more processed reception signals and the representative value signal, corresponding to each of the plurality of sampling times, and generating image data for a display using the plurality of differential signals.

12. The processing apparatus according to claim 11, wherein the threshold value is equal to or larger than 1% and equal to or smaller than 10% of a possible maximum amplitude of the plurality of data signals.

13. The processing apparatus according to claim 11, wherein the signal processor is configured to generate the representative value signal by averaging the data signals in the plurality of data signals that are other than the one or more processed reception signals.

14. The processing apparatus according to claim 11, wherein the signal processor is configured to generate the representative value signal of less than all of the data signals in the plurality of data signals that are other than the one or more processed reception signals.

15. The processing apparatus according to claim 11, wherein the representative value signal is a signal having a median value or a mode value among the data signals in the plurality of data signals that are other than the one or more processed reception signals.

16. The processing apparatus according to claim 11, wherein the plurality of reception elements is arranged in an arc shape or a hemispherical shape.

17. The processing apparatus according to claim 11, wherein the acoustic waves are photoacoustic waves generated by irradiating a subject with light.

18. The processing apparatus according to claim 11, wherein the acoustic waves are ultrasonic waves which are transmitted and are reflected in a subject.

19. The processing apparatus according to claim 11, wherein the signal processor is configured to add a flag indicating a magnitude relative to the threshold value to the one or more processed reception signals corresponding to each of the plurality of sampling times.

20. The processing apparatus according to claim 11, wherein the same time is a same time point.

* * * * *